(12) United States Patent
Xiao et al.

(10) Patent No.: US 9,612,221 B2
(45) Date of Patent: Apr. 4, 2017

(54) OPTO-ELECTROCHEMICAL SENSING SYSTEM FOR MONITORING AND CONTROLLING INDUSTRIAL FLUIDS

(71) Applicants: Chem-Aqua, Inc., Irving, TX (US); Pyxis Lab, Inc., Hopkinton, MA (US)

(72) Inventors: Caibin Xiao, Holliston, MA (US); Jackey Gu, Shanghai (CN); Scott M. Boyette, Irving, TX (US); Jerold Murray, Arlington, TX (US)

(73) Assignee: Chem-Aqua, Inc. + Pyxis Lab, Inc.

( * ) Notice: Subject to any disclaimer, the term of this patent is extended or adjusted under 35 U.S.C. 154(b) by 121 days.

(21) Appl. No.: 14/513,516

(22) Filed: Oct. 14, 2014

(65) Prior Publication Data

US 2016/0103089 A1 Apr. 14, 2016

(51) Int. Cl.
| | |
|---|---|
| *G01N 27/27* | (2006.01) |
| *G05D 7/06* | (2006.01) |
| *G01N 21/64* | (2006.01) |
| *G01N 21/51* | (2006.01) |
| *G01N 21/59* | (2006.01) |

(52) U.S. Cl.
CPC .......... *G01N 27/27* (2013.01); *G01N 21/645* (2013.01); *G01N 21/51* (2013.01); *G01N 21/59* (2013.01); *G01N 2021/6491* (2013.01); *G01N 2201/0221* (2013.01); *G01N 2201/062* (2013.01)

(58) Field of Classification Search
CPC .. G01N 27/27; G01N 21/64; G01N 2201/062; G05D 7/0623
USPC ...................................... 356/432–444, 39–41
See application file for complete search history.

(56) References Cited

U.S. PATENT DOCUMENTS

| | | | |
|---|---|---|---|
| 4,076,420 A | | 2/1978 | De Maeyer et al. |
| 4,112,741 A | | 9/1978 | Kerfoot et al. |
| 4,555,936 A | | 12/1985 | Scott |
| 4,783,314 A | | 11/1988 | Hoots et al. |
| 4,940,945 A | * | 7/1990 | Littlejohn .......... G01N 33/4925 204/406 |
| 4,992,380 A | | 2/1991 | Moriarty et al. |
| 5,068,542 A | * | 11/1991 | Ando .................... G01N 21/85 250/573 |
| 5,266,179 A | * | 11/1993 | Nankai ............ G01N 33/48771 204/401 |
| 5,304,800 A | | 4/1994 | Hoots et al. |
| 5,411,889 A | | 5/1995 | Hoots et al. |
| 5,435,969 A | | 7/1995 | Hoots et al. |
| 5,691,809 A | | 11/1997 | Tackett et al. |
| 5,999,250 A | | 12/1999 | Hairston et al. |
| 6,060,318 A | | 5/2000 | Moeggenborg et al. |
| 6,228,652 B1 | | 5/2001 | Rodriguez et al. |

(Continued)

*Primary Examiner* — Sang Nguyen
(74) *Attorney, Agent, or Firm* — Ross Barnes LLP; Robin L. Barnes; Monty L. Ross

(57) ABSTRACT

A system and method for controlling operating parameters of an industrial fluid system based on measurement of optical and electrochemical properties. The system comprises a handheld or portable meter that can substantially simultaneously measure one or more optical properties and one or more electrochemical properties of a sample of fluid from the fluid system. Information based upon the measurements or calculations made by the system may be used to manually or automatically alter various operating parameters to control the fluid system and aid in maintaining stable operation of the fluid system within preferred specifications.

40 Claims, 6 Drawing Sheets

(56) References Cited

U.S. PATENT DOCUMENTS

| | | |
|---|---|---|
| 6,280,635 B1 | 8/2001 | Moriarty et al. |
| 6,315,909 B1 | 11/2001 | Hoots et al. |
| 6,369,894 B1 | 4/2002 | Rasimas et al. |
| 6,618,934 B1 * | 9/2003 | Feldman ............... C12Q 1/001 29/593 |
| 6,662,636 B2 | 12/2003 | Shah et al. |
| 6,670,617 B2 | 12/2003 | Banks |
| 7,095,500 B2 | 8/2006 | Banks |
| 7,154,603 B2 | 12/2006 | Banks |
| 7,525,660 B2 | 4/2009 | Gigioli et al. |
| 7,550,746 B2 | 6/2009 | Tokhtuev et al. |
| 7,652,267 B2 | 1/2010 | Tokhtuev et al. |
| 7,989,780 B2 | 8/2011 | Tokhtuev et al. |
| 8,084,756 B2 | 12/2011 | Tokhtuev |
| 8,101,426 B2 | 1/2012 | Durack et al. |
| 8,248,611 B2 | 8/2012 | Christensen et al. |
| 8,269,193 B2 | 9/2012 | Christensen et al. |
| 8,352,207 B2 | 1/2013 | Tokhtuev et al. |
| 8,373,140 B2 | 2/2013 | Tokhtuev et al. |
| 8,440,062 B2 | 5/2013 | Kidwell |
| 8,654,319 B2 | 2/2014 | Rao et al. |
| 9,140,648 B2 | 9/2015 | Tokhtuev et al. |
| 2002/0127144 A1 * | 9/2002 | Mehta ............... G01N 15/1031 422/81 |
| 2008/0105566 A1 * | 5/2008 | Kitawaki ............... G01N 21/03 205/775 |
| 2011/0100820 A1 * | 5/2011 | Bachmann ........ B01L 3/502761 204/547 |
| 2014/0185031 A1 * | 7/2014 | Zhang ................... G01N 15/12 356/39 |
| 2015/0090900 A1 | 4/2015 | Banks et al. |

\* cited by examiner

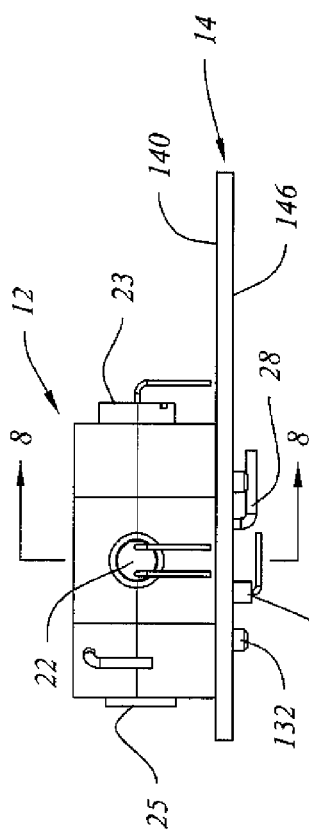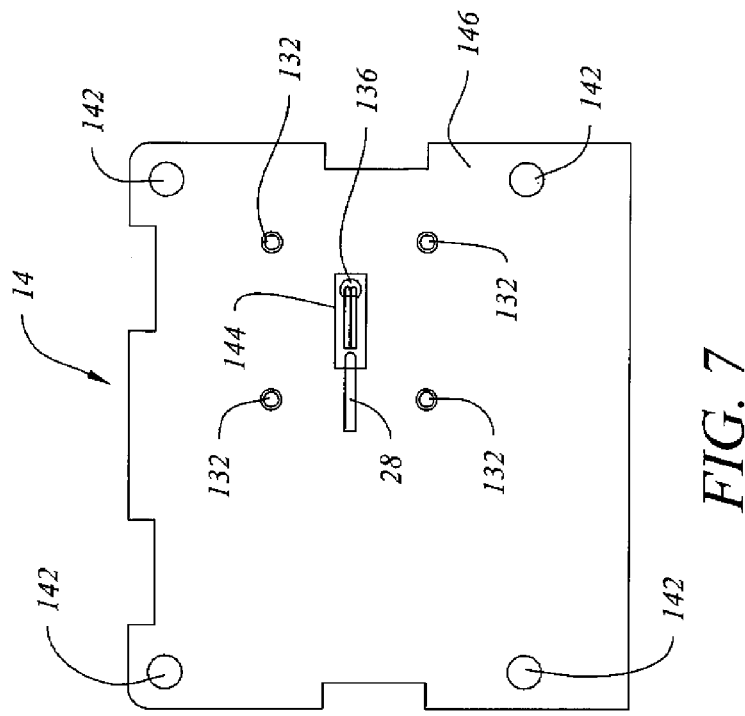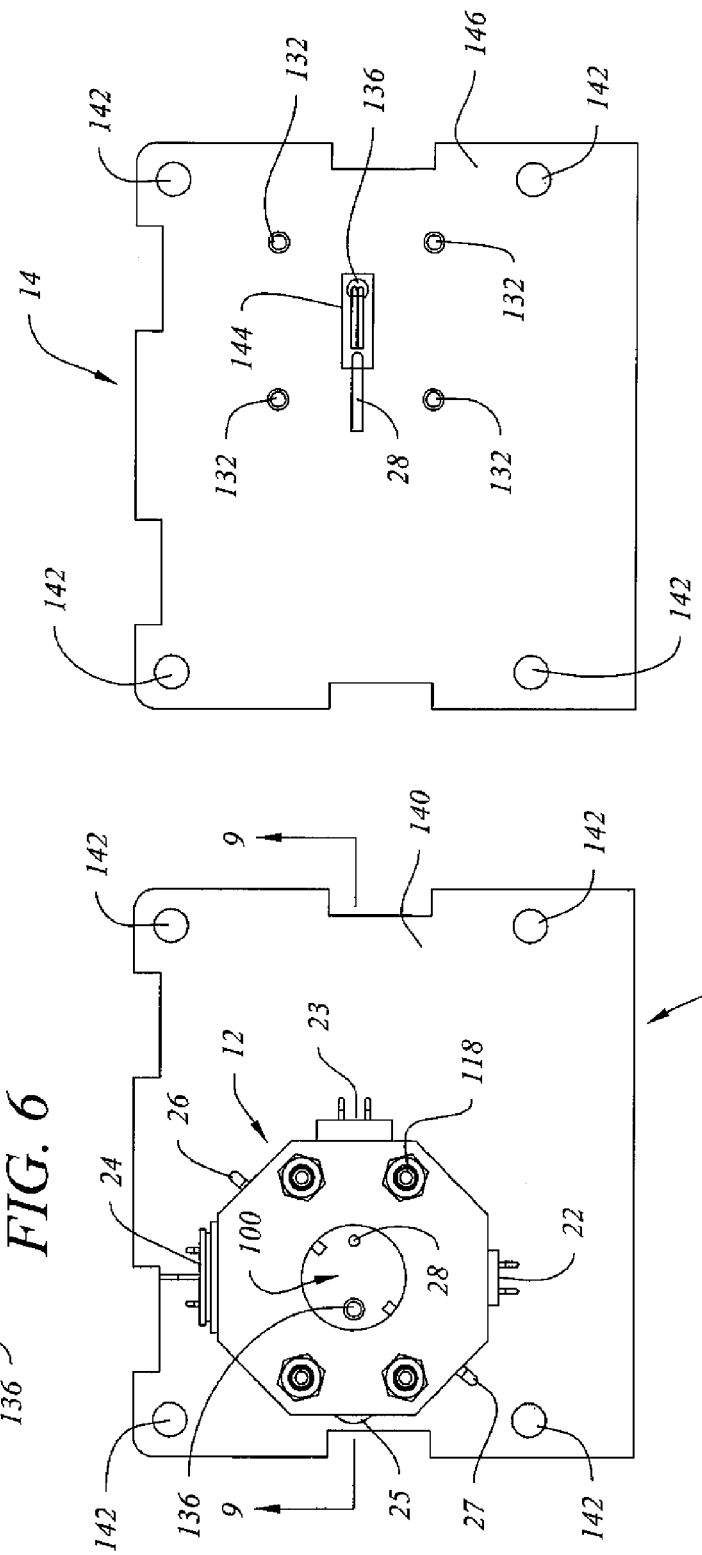

OPTO-ELECTROCHEMICAL SENSING SYSTEM FOR MONITORING AND CONTROLLING INDUSTRIAL FLUIDS

BACKGROUND OF THE INVENTION

1. Field of the Invention

This invention relates to measuring opto-electrochemical properties of a fluid or fluid mixture, or other properties of the fluid or fluid mixture based on the opto-electrochemical properties, using a simple integrated sensing cell. The system would be used to measure or calculate the properties of industrial fluids or fluid mixtures, and provide the necessary information to properly control the operation and treatment of an industrial fluid system.

2. Description of Related Art

Accurate measurement of various properties in industrial fluid systems, such as cooling towers and boiler systems, is required to assure proper performance, safety, and reliability of the fluid system, and to reduce unit lifetime costs of components in the fluid system. There are numerous sensing methods used to measure process fluids, but two of the more common are optical and electrochemical. Typically, measurement of an optical property, such as fluorescence, absorbance, or transmission, and measurement of an electrochemical property, such as conductivity, involves the use of two separate measurement instruments and two separate samples from the fluid system. For example, a fluorometer and a conductivity meter may be used in series, as described in U.S. Pat. No. 4,112,741, to measure optical and electrochemical properties in a body of water. As additional examples, U.S. Pat. Nos. 4,783,314 and 6,369,894 disclose the fluorometric measurement of the concentration of a fluorescent tracer included in a treatment product added to an industrial fluid system, which is indicative of the concentration of the treatment product in the fluid system, in conjunction with a separate conductivity meter used in the fluid system. The results of these measurements may then be used to adjust various operating parameters within the fluid system in order to control the fluid system. Other methods and devices are known for using data from various measured properties to control a fluid system. For example, U.S. Pat. No. 6,280,635 discloses the use of fluorescence and make-up water composition to control a cooling tower. A complex matrix control platform is disclosed in U.S. Pat. No. 6,315,909, where separately measured conductivity and fluorescence are two tools that may be used to make adjustments to the fluid system.

It is also known to conduct fluorometric and conductivity measurements on the same sample of water, but using a fluorometer and a separate conductivity meter that are not integrated into a single, hand-held device. For example, U.S. Pat. No. 5,691,809 discloses a system to monitor fluid phase changes in processing of crude oil and other organic liquids. The system in the '809 patent uses a heated, pressurized cell containing a sample of the liquid to be analyzed in contact with electrodes. The cell is connected to a fiber optic probe and fluorometer external to the cell and to an external conductivity meter. Additionally, the conductance is measure by a disk electrode and the pressure cell body. This configuration is known to lack sensitivity as demonstrated in FIG. 5 of the '809 patent, where the range of change is small, and would be insufficient for monitoring most industrial process fluids.

More complex instruments that combine fluorometric and conductivity or other electrochemical property measurements into a single device are also known. For example, dip-type or immersion-type sensors are disclosed in U.S. Pat. Nos. 7,550,746 and 8,440,062 for measuring fluorescence and conductivity. These instruments are immersed into the water being tested, which may result in inaccurate measurements. The complexity of the multi-component sensor system in the '062 patent also requires the conductance electrodes to be floated while taking measurements with the other electrochemical electrodes, creating a risk of inaccurate bridge balance when making a conductance measurement. A flow-through sample cell instrument for measuring fluorescence, absorption, and conductivity is disclosed in U.S. Pat. No. 4,555,936. The electrodes act as inlet and outlet flow conduits for the sample to pass through the sample cell. Measuring conductivity with flowing fluid, and where mixing in a square cell configuration, would be prone to errors.

Measuring conductivity and fluorescence in blood samples is also disclosed in U.S. Pat. No. 6,228,652. The instrument disclosed in the '652 patent uses a standard configuration for fluorescence measurements, but with a multitude of filters, mirrors, and photomultiplier tubes. The conductance measurement uses two electrodes, but it measures radio frequency (RF) Conductance where the conductivity is proportional to the dissipation of the RF power. This was designed to measure the conductance inside the blood cell, and it requires that the field be focused at the small cell window where the single cell is being measured. Additionally, the sample cell is a cytometric flow-through cell designed to allow blood cells to pass through one at a time. The measurement approach disclosed in the '652 patent would be inappropriate for a bulk fluid or fluid mixtures.

Several prior art instruments utilize multiple photodetectors and a single light source to measure multiple optical properties or improve upon fluorescence detection. For example, the '936 patent measures fluorescence and absorbance and U.S. Pat. No. 7,652,267 measures fluorescence and turbidity. A second photodetector in the '267 and '894 patents may also be used as a reference detector to measure UV intensity to provide correction of the fluorescent signal. Additional photodetectors are also disclosed in the '652 patent to correspond to the number of fluorescence spectra emitted by the dyes and fluorochromes in the sample. Two light sources are also disclosed in U.S. Pat. No. 7,095,500, one being an excitation light source and a second light source that does not induce fluorescence, but is used to correct for effects on the fluorescent measurement due to fouling or turbidity. To provide measurements of additional optical properties, multiple instruments may be stacked together in a modular device or have interchangeable parts. For example, the '894 patent discloses stacking between two and sixteen modular flourometers, each having a flow-through sample cell, a light source, and two photodetectors to measure fluorescence of different species when the water sample contains multiple species with different emission spectra. The '500 patent discloses an interchangeable probe tip with each tip having a different optical configuration to measure different properties, such as fluorescence and absorbance, so that the tips have to be changed out between measurements to measure both properties.

None of the known references disclose a single unit having multiple light sources and multiple optical detectors to measure multiple properties on a single sample contained within a sample cell. Additionally none of the known references disclose combining optical property detection with detection of multiple electrochemical properties, through the use of two or more electrodes, in a single device. Nor do any of the known references disclose comparing the results of an optical measurement with an electrochemical measurement obtained by a single device to enhance the control of a fluid system. There is a need for a simple, integrated, hand-held system that is capable of accurately measuring and calculating multiple properties of a fluid sample based on optical and electrochemical data or signals from a single sample. There is also a need for a system and method that can improve the operation of a fluid system by using data from at least one optical property-based measurement and at least one electrochemical property-based measurement to control operating parameters of the fluid system.

SUMMARY OF THE INVENTION

This invention provides a system and method to determine properties of a fluid or fluid mixture based on both optical and electrochemical measurements of a sample and to control the operating parameters of a fluid system based on those properties. A sensing system according to a preferred embodiment of the invention can be used to rapidly and accurately measure the opto-electrochemical properties of a fluid or fluid mixture and comprises a sample cell and integrated optical and electrical components in a portable, handheld device. The system can be configured to determine various fluid properties of a sample using fluorescence, absorbance, transmission, or any other light-based measurement technique. The system can also be configured to substantially simultaneously determine various fluid properties of the same sample using integrated electrochemical components to measure conductivity, cyclic voltammetry, open circuit potential, or oxidation-reduction potentials.

A sensing system according to a preferred embodiment of the invention comprises a sample cell, at least one light source configured to direct light through a sample in the sample cell, at least one an optical sensor, at least two electrodes partially disposed in contact with the sample, an electronic module that controls the testing/measuring and for processing data received from the optical sensor and electrodes, and a small, handheld housing enclosing the sample cell, light source, optical sensor, electrodes, and electronic module. The housing preferably allows the sample to be added to the sample cell through a port in the housing, allowing the outside of the housing to be wetted but protecting the electronic module or other sensitive internal components of the sensing system. After adding a sample from a fluid system to the sample cell through the port in the housing, the sample is tested within the sample cell using a selected test configuration of the particular version of device (based on the various properties to be measured), and the sample could be eliminated from the sensing system by inverting the device so that the sample is drained from sample cell by gravity. Repeat measurements could be made by simply adding a new sample to the sample cell of the device, and different fluids could be measured using the same sample cell. Most preferably, the sample cell is rinsed a few times with water (deionized or distilled, preferably) or with a portion of the next sample to be measured. The sensing system is designed to be portable and powered by batteries, solar panels, DC or other portable power sources. The sensing system does not require the use of pumps or chemical injection to perform the various opto-electrochemical tests. Additionally, the preferred use of a sample cell to temporarily contain a sample to be tested eliminates inaccuracy problems associated with dip or immersion-type sensors or flow cell sensors.

According to a preferred embodiment, a sensing system is configured to detect the transmission or emission of light from one or more light sources through a sample or from a compound in a sample using one or more optical detectors and to measure a change of electric potential between electrodes in contact with the sample. Data or signals from the optical sensor or sensors and electrodes are received by an electronic module that is programmed to calculate at least one property, and preferably at least two properties, of the fluid in the sample. The properties calculated based on data or signals from the optical sensor or sensors may include an optical property, such as fluorescence, transmission, absorbance, or turbidity, or may be an interpretation, correlation or further manipulation of such optical property to determine a concentration of a tracer compound in the sample (such as a fluorescent tracer included in a treatment product added to the fluid system from which the sample is obtained) or a concentration of a treatment product or other chemical in the sample. The properties calculated based on data or signals from the electrodes may include electrochemical properties, such as conductivity, oxidation-reduction potential (with the appropriate isolation bridge if necessary), or may be an interpretation, correlation or further manipulation of such optical property to determine a concentration of a treatment product or other chemical in the sample.

According to another preferred embodiment, information regarding the measured or calculated properties of the fluid sample is used to control operating parameters of a fluid system from which the sample was obtained. The operating parameters (such as rate or amount of treatment product(s) added, "fresh" water or fluid added, blowdown, feed or other fluid system adjustments) may be altered (such as by opening or closing valves in the fluid system, operating pumps, or through manual addition of treatment products or chemicals) if the information indicates a change is needed, such as when the calculated value of a property falls outside a specified range for that property or is above or below a pre-set threshold value for that property. Additionally, calculated values may be compared and the difference may indicate a need to alter or automatically trigger an alteration in operating parameters for the fluid system, which may improve accuracy in controlling the fluid system.

A sensing system according to another preferred embodiment of the invention comprises an electronic module with processing capabilities that allow it to send and receive signals, make calculations, display data, store data and/or save data to a removable memory card or other connected device, and process one or more tests that are selected by a user (such as testing conductivity and fluorescence of a sample). A preferred electronic module is also capable of automatically sending signals to alter one or more operating parameters of the fluid system(s), making recommendations for altering operating parameters, and accepting manual input of operating parameter changes and sending signals to other devices or equipment to carry out the manually input changes, in order to control operation of the fluid system. The information provided by the sensing system may be displayed on a screen on the sensing system housing, thereby allowing the user to make manual changes to the fluid system based on the information, such as manually adjusting a valve, to manually input instructions into the sensing system meter which are then sent to other devices or equipment or to manually input instructions into a separate electronic control system to make changes to the fluid system based on the information. The information may also be communicated to a separate or remote control system, directly (through a plug-in connection) or by wireless communication, to remote users (such as supervisors or remote operators), to achieve automated control over the fluid system. The sensing system is preferably part of a larger control system with numerous configurations of applied electronics, and this would allow a multitude of optical and electrochemical measurements, and the ability to communicate data from the sensing system to computers or other instruments in order to control operation of a fluid system.

According to another preferred embodiment, an alarm signal, such as an audible signal, a visual signal or both, may be generated when a calculated property or value is outside a given range or below or greater than a pre-set value. The alarm signal may be generated by the portable meter and may be communicated wirelessly to a remote control system, computer screen, or user's/supervisor's cell phone or email. According to yet another preferred embodiment, additional alarm signals may also be generated when a calculated property or value is within one or more ranges or above or below one or more pre-set values for that property. These additional alarm signals may alert a user when a property is approaching a value that would require a change in an operating parameter or when the value is at a critical level requiring immediate attention. Preferably, the additional alarm signals are audibly or visually distinct from each other.

BRIEF DESCRIPTION OF THE DRAWINGS

The system of the invention is further described and explained in relation to the following drawing wherein:

FIG. 5 is a top plan view of the opto-electrical housing and printed circuit board of FIG. 3;

FIG. 6 is a side elevation view of the opto-electrical housing and printed circuit board of FIG. 3;

FIG. 7 is a bottom plan view of the printed circuit board of FIG. 3;

DESCRIPTION OF THE PREFERRED EMBODIMENTS

Figure 1:
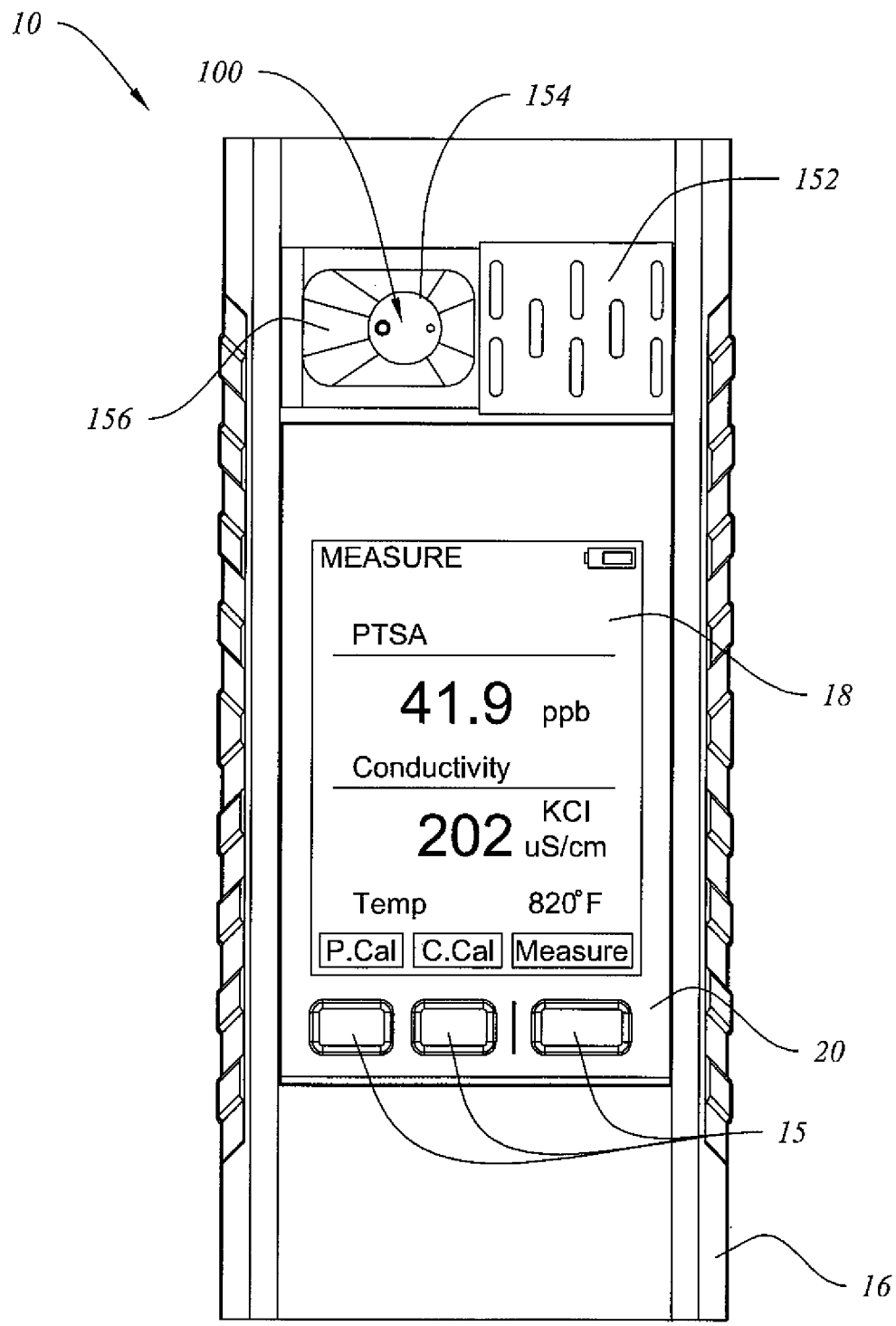
FIG. 1 is a top plan view of an electrochemical-optical sensing device according to a preferred embodiment of the invention.

FIGS. 1-9 depict an electrochemical-optical sensing system 10 according to a preferred embodiment of the invention. Electrochemical-optical sensing system 10 preferably comprises electro-optical housing 12, printed circuit board 14, external housing 16, display 18, control panel 20, a sample receptacle for containing a sample of water or other fluid to be analyzed and formed at least in part by sample cell 80 and portions of electro-optical housing 12, at least one light source 22 (and most preferably two light sources 22, 23), at least one optical detector or sensor 24 (and most preferably two optical detectors or sensors 24, 25), and at least two electrodes 26, 27 that allow optical measurements and electrochemical measurements of the sample. The specific model shown in FIGS. 1-9 is designed to measure conductivity and fluorescence of aqueous process fluid samples obtained from a fluid system, such as a cooling tower or a boiler system. Conductivity is a common way to measure the cycles of concentration in cooling and softened water boiler systems because of the ionic strength in the make-up water. Treatment chemicals, frequently containing an added fluorescent tracer, are added to such fluid systems to control corrosion and fouling. A fluorescent signal from the tracer may be used to indicate the concentration of treatment chemical in the fluid system. Modifications of the configuration shown in FIGS. 1-9 to measure other optical or electrochemical properties will be understood by those of ordinary skill in the art.

Figure 2:
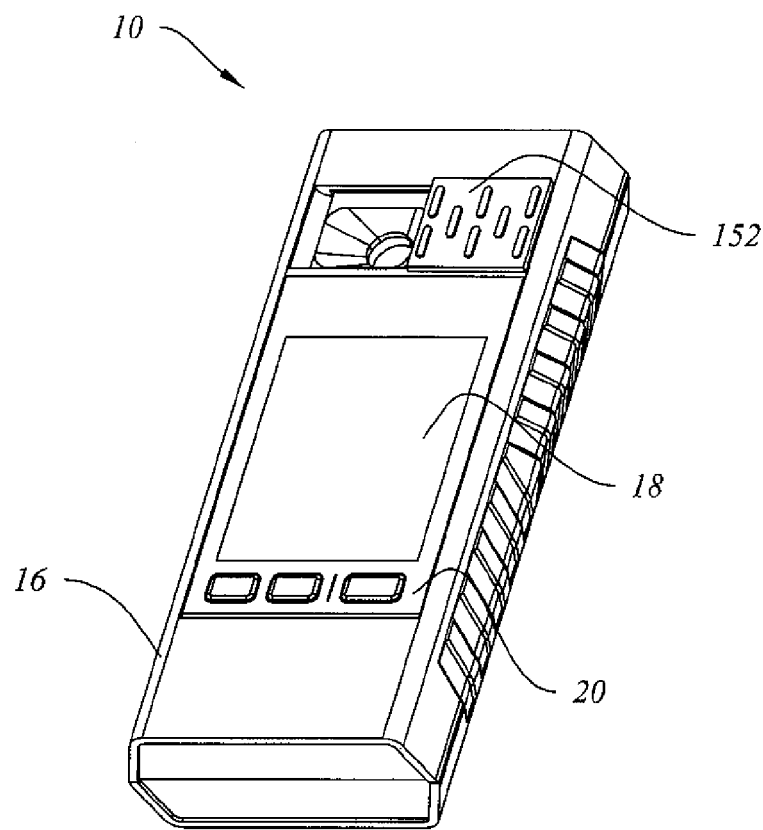
FIG. 2 is a perspective view of the electro-optical sensing device of FIG. 1.
Figure 3:
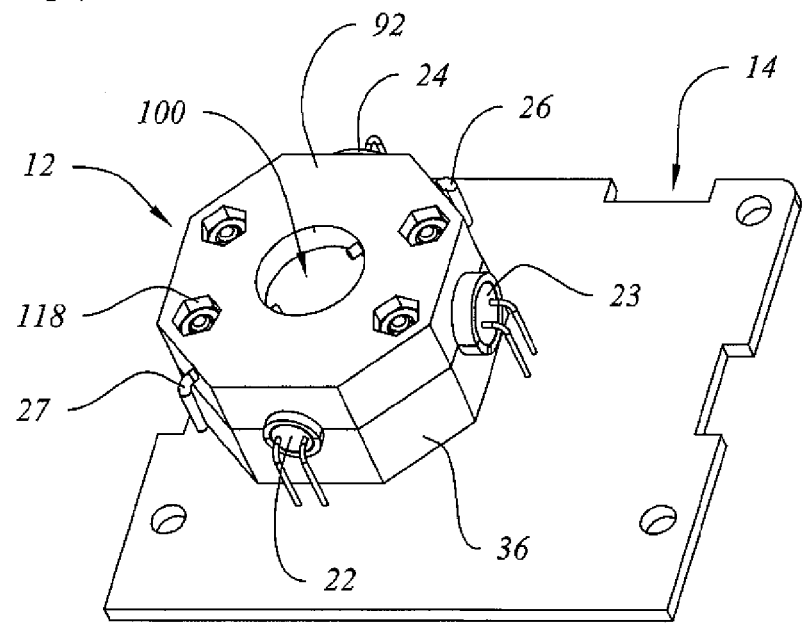
FIG. 3 is top-down, front perspective view of an opto-electrical housing and printed circuit board according to a preferred embodiment of the invention.
Figure 4:
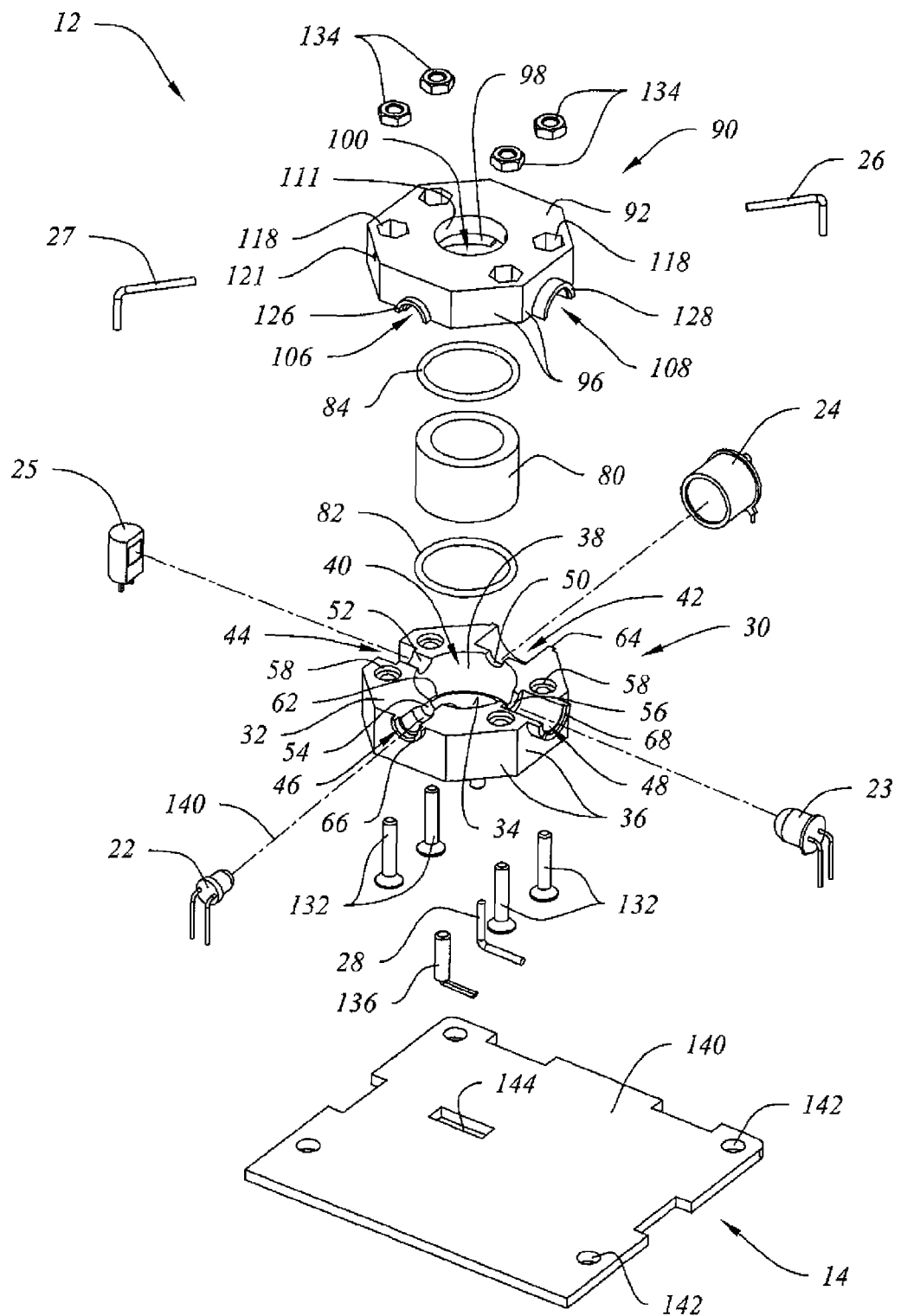
FIG. 4 is an exploded perspective view of the opto-electrical housing and printed circuit board of FIG. 3.
Figure 8:
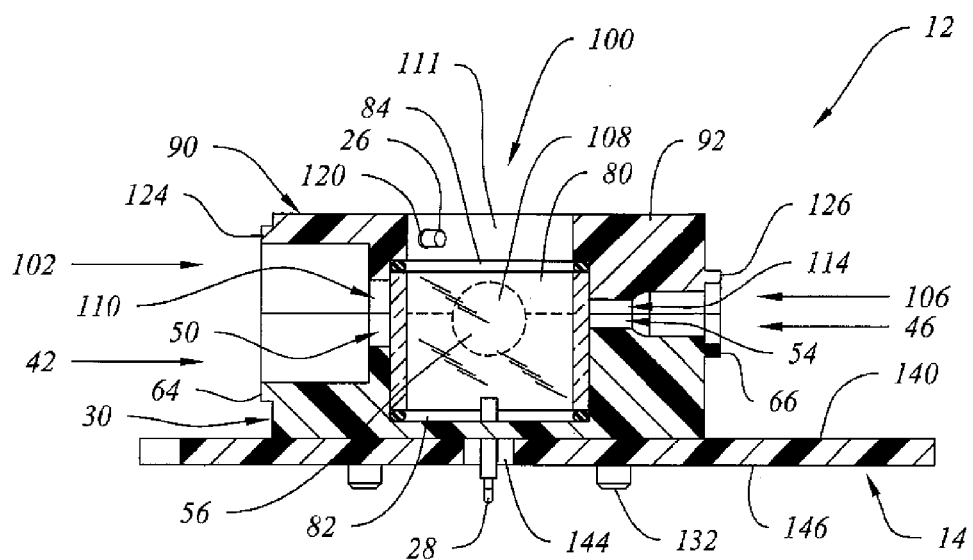
FIG. 8 is a side elevation cross-sectional view of the opto-electrical housing and printed circuit board of FIG. 6.
Figure 9:
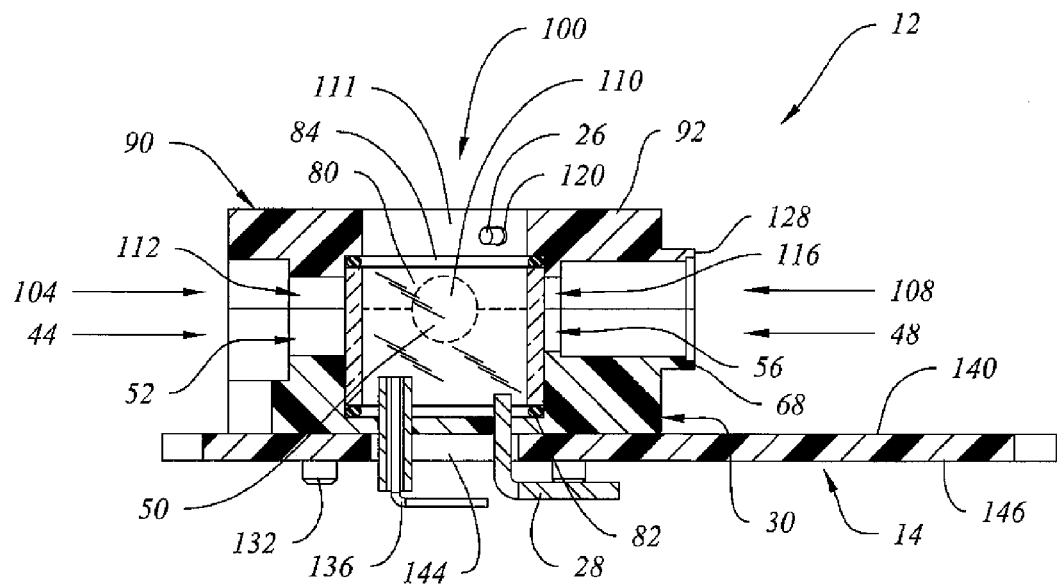
FIG. 9 is a side elevation cross-sectional view of the opto-electrical housing and printed circuit board of FIG. 5.

FIGS. 1-2 depict a preferred embodiment of external housing 16, display 18, and control panel 20. External housing 16 preferably contains and protects the light sources 22, 23, optical sensors 24, 25, and an electronic module (including printed circuit board 14). Sample cell 80 (shown on FIG. 4) is accessible through port 154 disposed on an upper surface of housing 16 and through opening 100 of electro-optical housing 12. Port 154 is preferably surrounded by a recessed area 156 that forms a trough for the sample of water or other fluid being analyzed so that the sample overflows the volume available in sample cell 80 and the internal volume of opening 100 above sample cell 80. This helps ensure that there is a sufficient sample size for testing and that the sample comes into contact with electrodes 26, 27, which are preferably disposed through upper body 90 of electro-optical housing 12 at a location above an upper edge of sample cell 80. Recessed area 156 is shown as a segmented area around port 154 in FIG. 1, but a smooth surface and other shape configurations may also be used. Most preferably, various parts of system 10, including sample cell 80, the internal volume of space within opening 100 above sample cell 80, and recessed area 156, cooperate to form a sample receptacle for containing the sample of fluid to be tested; however, other configurations for a sample receptacle may also be used. Port 154 and recessed area 156 are preferably sealed and cooperate with sealing rings 82 and 84, and other seals around electrodes 26, 27, 28 and temperature sensor 136, to maintain the sample of water or other fluid within the test area of the sample receptacle and to prevent the sample of water or other fluid from otherwise entering external housing 16 or electro-optical housing 12 or contacting sensitive portions of the electronic module. An optional door or covering 152 may be used to cover port 154 and recessed area 156 when system 10 is not in use or when an analysis of a sample is being performed by system 10. Most preferably, door 152 is a sliding door, but other configurations, such as a hinged door, may also be used. This optional door 152 may block out ambient light that may interfere with detection of certain optical properties. A display 18 provides a visual representation of analysis results, calculations, and/or data regarding the analysis or calculations performed by system 10. As shown in FIG. 1, system 10 may display conductivity measurements and a concentration of a tracer included in a treatment product added to the fluid system, for example. The electronic module may be programmed to display other properties of the fluid, such as a calculated concentration of the treatment product (rather than the tracer concentration), and may be programmed to display measurements in different units. Control panel 20 preferably includes a plurality of buttons 15 or a touch screen that permits the user to provide inputs to system 10, such as selection of the particular test to be performed, information to designate the sample, recall of stored data from prior tests, or sending electronic commands to other devices or components of the fluid system being tested or a control system that controls various components of the fluid system. In conjunction with the electronic module, the display 18 and control panel 20 may be programmed for a variety of functions as will be understood by those of ordinary skill in the art.

External housing 16 is preferably substantially rectangular and compact in size so that it is easily hand-carried and held by one hand. Most preferably, external housing 16 has a length dimension less than about 10 inches, a width dimension less than about 5 inches, and a height dimension in less than about 3 inches. External housing 16 also preferably includes various ports (such as a USB port) to connect system 10 to other devices (such as a computer or server), to an external power source, and may include one or more slots for removable memory cards. These ports would interact with the electronic module of the system 10 according to known methods understood by those of ordinary skill in the art.

As shown in FIGS. 3-9, electro-optical housing 12 preferably comprises a lower optical module holder body 30, an upper optical module holder body 90, a sample cell 80, light sources 22, 23, optical detectors 24, 25, and electrodes 26, 27, 28. Lower body 30 and upper body 90 are preferably similarly shaped and designed to mate together to hold other parts of system 10, such as first LED 22, first photodiode 24, and sample cell 80, in position in system 10. Lower body 30 and upper body 90 are depicted as octagon shaped, but other shapes, such as a circular shape, may be used. For ease of viewing lower body 30 and upper body 90 as mated together and relative to printed circuit board 14, the cross-sectional views in FIGS. 8-9 do not depict light sources 22, 23 or optical detectors 24, 25 as shown in FIGS. 3-6.

Lower body 30 preferably comprises an upper surface 32, lower surface 34, exterior or outer sidewalls 36, and substantially cylindrical interior or inner sidewall 38. Annular opening 40 is formed by interior sidewall. 38 and preferably extends from upper facing surface 32 through to lower surface 34, being open at surface 32 and sealed at surface 34. Annular opening 40 serves as a receptacle for a lower end of sample cell 80, having a diameter slightly larger than sample cell 80 so that sample cell 80 fits snugly within opening 40. Slots 42, 44, 46, and 48 extend from outer sidewall 36 toward inner sidewall 38 and are configured to support light sources 24, 25, and optical detectors 22, 23, respectively. Most preferably, slots 42, 44, 46, and 48 are shaped to conform to a lower portion of the particular light source or optical detector that will be supported by the slot. Depending on the type and shape of the light source or detector supported by the slots, protrusions, such as 64, 66, and 68, may be provided to aid in supporting the light source or detector relative to lower body 30 and system 10. A cutout 50, 52, 54, and 56 extends from an interior end of each slot 42, 44, 46, and 48, respectively, through to interior sidewall 38. Lower body also preferably comprises a plurality of mounting apertures 58, extending from upper surface 32 through lower surface 34. Each mounting aperture 58 is preferably configured to receive a mounting bolt 132. Two apertures are preferably disposed through a central portion of lower surface 34 to allow insertion of electrode 28 and temperature sensor 136 into sample cell 80.

Upper body 90 preferably comprises an upper surface 92, exterior or outer sidewalls 96, and two substantially cylindrical interior or inner sidewalls 98 and 111. Annular opening 100 is formed by interior sidewall 111. Sidewall 111 is smaller in diameter than sidewall 98, forming a shoulder at a transition point between sidewalls 98 and 111 that is configured to receive an upper end of sample cell 80 and secure it within upper body 90. Opening 110 is preferably open all the way through from upper surface 92 through to an interior of sample cell 80. The diameter of sidewall 98 is slightly larger than sample cell 80 so that sample cell 80 fits snugly within upper body 90. The smaller diameter of sidewall 111 and the shoulder formed between sidewalls 98 and 111 serve to retain sample cell 80 within system 10 when it is inverted to empty sample cell 80, as described below. Slots 102, 104, 106, and 108 extend from outer sidewall 96 toward inner sidewall 98 and are configured to hold light sources 24, 25, and optical detectors 22, 23, respectively, in position relative to other parts of system 10. Most preferably, slots 102, 104, 106, and 108 are shaped to conform to an upper portion of the particular light source or optical detector that will be held by the slot. Depending on the type and shape of the light source or detector held by the slots, protrusions, such as 124, 126, and 128, may be provided to aid in securing the light source or detector relative to upper body 30 and system 10. A cutout 110, 112, 114, and 116 extends from an interior end of each slot 102, 104, 106, and 108, respectively, through to interior sidewall 98. Upper body 90 also preferably comprises a plurality of mounting apertures 118, a second electrode aperture 120, and a third electrode aperture 121. Mounting apertures 118 extend from upper surface 92 through a lower surface of upper body 90. A lower end of each mounting aperture 118 is preferably configured to receive a mounting bolt 132 and an upper end of each mounting aperture 118 is preferably configured to receive a mounting nut 134, so that an upper end of each mounting nut 134 does not protrude substantially above upper surface 92 when secured to a bolt 132. Second electrode aperture 120 is preferably positioned around an outer perimeter of upper body 90 substantially opposite (or around 180° from) third electrode aperture 121. Electrode apertures 120, 121 are disposed through sidewall 96 to interior sidewall 111. Electrode aperture 120 is configured to receive electrode 26 and aperture 121 is configured to receive electrode 27.

The slots on lower body 30 preferably align and cooperate with the slots in upper body 90 to support and secure two light sources and two optical detectors in position within electro-optical housing 12 relative to sample cell 80. For example, slots 42 and 102 are shaped and aligned to receive a first photodiode 24; slots 44 and 104 are shaped and aligned to receive a second photodiode 25; slots 46 and 106 are shaped and aligned to receive a first LED 22; and slots 48 and 108 are shaped and aligned to receive a second LED 23. Similarly, the cutouts in lower body 30 align and cooperate with the cutouts in upper body 90 to form an optical window for each light source and each detector. For example, cutouts 50 and 110 align to form a window for first photodiode 24; cutouts 52 and 112 align to form a window for second photodiode 25; cutouts 54 and 114 align to form a window for first LED 22; and cutouts 56 and 116 align to form a window for second LED 23. These cutouts preferably align to form circular or substantially circular openings or optical windows through which light may be emitted from light sources 22, 23 through sample cell 80, and then emitted or transmitted light detected or received by detectors 24, 25. The slots, cutouts, light sources, and optical detectors are preferably positioned in electro-optical housing 12 so that light may be emitted or transmitted and detected through a substantially central portion of sample cell 80. The shapes and sizes of these slots and cutouts may vary depending on the specific light source and optical detector used.

Optical sensors or detectors 24, 25 and light sources 22, 23 are preferably disposed between lower body 30 and upper body 90, within slots 42, 44, 46, 48, 102, 104, 106, and 108 as described above, and are positioned in spaced-apart locations around an outer perimeter of bodies 30, 90. Most preferably, they are located around the outer perimeter relative to each other (and a central axis, shown as 140 in FIG. 4, extending through lower body 30) so that a first light source 22 is positioned at a location equivalent to substantially 0°, a second light source 23 is positioned at a location equivalent to substantially 90°, a first optical detector 24 is positioned at a location equivalent to substantially 180°, and a second optical detector 25 is positioned at a location equivalent to substantially 270°. Depending on the type of light source and detector used and the type of optical measurement to be made, a detector may be located opposite (180° apart) the light source from which it will detect light or it may be at a right angle (90° apart), such as for detection of fluorescence where the optical sensor is at a right angle to the excitation source. Optical detectors 24, 25 are preferably a first and second photodiodes, most preferably both silicon photodiodes. Other types of photodiodes or optical detectors such as gallium phosphide or silicon photomultiplier, may be used, depending on the type of measurement to be made, type of light source used, and other factors, as will be understood by those of ordinary skill in the art. Light sources 22, 23 are preferably first and second LEDs. First LED 22 is preferably a UV LED emitting light in a wavelength range of 250 to 450 nm and second LED 25 is preferably an LED emitting light in a wavelength range of 400 to 1100 nm. Other types of light sources and wavelengths may be used, depending on the type of measurement to be made, as will be understood by those of ordinary skill in the art.

As an example, system 10 may be configured so that a beam of light from one light source (LED 23) contacts a sample within sample cell 80, excites electrons in fluorescent molecules within the sample, and the fluorescent emission is detected by a detector located approximately 90° from the light source (photodiode 24). The other light source (LED 22) may emit light at a different wavelength and be detected by a photodetector (photodiode 24) located approximately 180° from the light source or by a photodetector (photodiode 25) located approximately 90° from the light source to measure other optical properties, such as absorbance or turbidity. Other optical measurements may also be made using the light sources and detectors, with each detector capable of measuring a property from the light source located approximately 90° from the detector and a different property from the light source located approximately 180° from the detector. For example, detector 24 may be used to measure fluorescence excited by LED 23 and also used to measure the optical density of LED 22. Detector 25 may be used to measure light scattering excited by LED 22. The same detector 25 is used to measure the optical density of the LED 23. Measuring multiple properties with system 10 allows for compensation or corrections of measurements based on variations in the sample, such as color and turbidity.

Other types of LEDs or light sources may be used depending on the type of measurement to be made, type of detector used, and other factors, as will be understood by those of ordinary skill in the art. Light sources and detectors used with electro-optical housing 12 are preferably commercially available products and it is not necessary to use specialized or customized optical components with system 10. Although it is preferred to include two light sources and two detectors in system 10 to increase functionality, a single light source or single detector may be used. Additionally, other components that are well known in the art may also be incorporated into electro-optical housing 12 (or the light source or detector) to facilitate certain optical measurements, such as filters and mirrors. For example, fluorescence detection would require necessary bandpass filters to isolate the excitation light from the emission signal.

A sample cell or sample tube 80 is provided for containing all or a portion of the sample of water or other fluid to be tested or analyzed with system 10. Sample cell 80 is preferably made of quartz, but other materials (such as glass) that are suitable for optical sensing and will not interfere with light transmission through the sample cell, may also be used. Sample cell 80 is preferably substantially cylindrical, with an open top or partially open top and an open bottom, and sized to provide a sufficient volume of water or other fluid to be analyzed. Other shapes may be used for sample cell 80 with corresponding changes to the shapes of other components of electro-optical housing 12, such as openings 40 and 100, to accommodate sample cell 80 within bodies 30, 90.

Disposed at a lower end of opening 40, on an interior side of lower surface 34, is an annular lip or groove 62. Annular lip 62 holds a first sealing ring 82, preferably an o-ring made of plastic or rubber, in position relative to sample cell 80 and lower surface 34. A second sealing ring 84 is positioned on a top surface of sample cell 80. The first and second sealing rings 82, 84 are preferably made from the same material and are the same size, but different sealing rings may also be used. The smaller diameter portion of opening 100 serves to retain sealing ring 84 in position on an upper end of sample cell 80. The sealing rings 82, 84 provide cushion for sample cell 80 between lower body 30 and upper body 90 and serve to prevent water or other fluid from leaking out of sample cell 80 into other parts of electro-optical housing 12 or system 10. Other known sealing mechanisms may also be used to create a fluid-tight seal around the sample of water or other fluid being analyzed to prevent it from contacting interior portions of system 10 (other than an interior of sample cell 80).

Alternatively, sample cell 80 may have a sealed bottom end so that lower surface 34 and sealing ring 82 are not necessary, with sample cell 80 being supported within electro-optical housing 12 by annular lip 62 or other supporting structure. Electrode 28 would be disposed through the bottom end of the sample cell in that configuration. As an additional alternative, the sample cell may be removable from sensing system 10. In a removable configuration, the sample cell is preferably an optically transparent cell overmolded onto metal electrodes that would connect to the electrochemical components of sensing system 10.

Most preferably, sample cell 80 is sized to have an internal volume between 1 to 20 mL. An additional 5 to 10 mL of fluid to be analyzed may be contained within the internal volume of opening 100 above sample cell 80. System 10 may also be configured so that a sample receptacle is formed solely by sample cell 80, by having sample cell 80 extend up to the top or through the top surface 92 of upper body 90 and without or without recessed area 156.

A temperature sensor 136 is preferably disposed through lower surface 34 and partially extends into sample cell 80 to contact the sample in sample cell 80. Alternatively, temperature sensor 136 may be flush with lower surface 34 of lower body 30 to measure the temperature of the sample within sample cell 80 or may be embedded in sample cell 80 or lower surface 34 in a manner allowing a temperature measurement of the sample in sample cell 80. In those alternate configurations, preferably, lower surface 34 is made of a material and thickness that will not substantially interfere with measurement of the temperature of the sample. Electrode 28 is also disposed through aperture 60 to contact the sample in sample cell 80. Additional electrodes 26, 27 are disposed through apertures 120, 121 to contact the sample in the area of opening 100 above sample cell 80. In the alternative embodiment where sample cell 80 extends up to the top or through the top surface 92, electrodes 26, 27 may be disposed through a sidewall of sample cell 80. As an additional alternative, either or both electrodes 26, 27 may be disposed through bottom surface 34, similar to electrode 28. As yet another alternative, electrodes 26, 27 may be disposed in a lid or cap on sample cell 80 or on port 154 or door 152 (if in a hinged-type configuration), so that they contact the sample once the lid or cap or door is closed. It is preferred that electrodes 26, 27, and 28 not be located directly within the light paths for light sources 22, 23 and do not interfere with or block the optical detection path. In another preferred embodiment, one or more of the electrodes are created as a coating on the exterior of the optical elements, but these coatings do not block the optical detection path. Appropriate sealing mechanisms, such a malleable material disposed around various components and openings, are used to create a fluid-tight seal around electrodes 26, 27, 28, and temperature sensor 136 if disposed through lower surface 34, as will be understood by those of ordinary skill in the art.

Two of the electrodes, preferably 26, 27 are used to measure the conductance of the fluid sample by applying a voltage and measuring the drop in voltage caused by the resistance in the sample. Similarly, oxidation and reduction potentials (ORP) or voltammetry may also be measured with one electrode (e.g. 26) acting as a working electrode, another electrode (e.g. 27) acting as a counter electrode, and the third electrode (e.g. 28) acting as a reference electrode. Different materials for each electrode may be used, depending on the specific types of electrochemical properties to be measured with system 10. For example, it is preferred that one electrode comprise golden or platinum and a second electrode is an Ag/AgCl reference electrode for measuring ORP. Other configurations and an optional fourth electrode may be used, as will be understood by those of ordinary skill in the art.

Mounting bolts 132 are preferably connected to printed circuit board 14 using conventional methods of connection. Mounting bolts 132 and nuts 134 cooperate to secure lower body 30 to upper body 90, holding the light sources 22, 23 and detectors 24, 25, and sample cell 80 in position within electro-optical housing 12, and to secure electro-optical housing 12 to printed circuit board 14. Printed circuit board 14 preferably comprises an upper surface 140, lower surface 146, and an aperture 144 through which electrode 28 and temperature sensor 136 are disposed (as shown in FIGS. 6-7). Other conventional attachment mechanisms may be used to connect lower body 30 to upper body 90, but they are preferably releasably attached so that parts within electro-optical housing 12 may be replaced or repaired as needed. Printed circuit board 14 is preferably connected to external housing 16 using conventional attachment mechanisms, such as nuts and bolts. Mounting apertures 142 may be used to secure printed circuit board 14 to external housing 16.

Printed circuit board 14 is part of an electronic module for system 10 and is used to connect the electronic components, such as the light sources 22, 23, detectors 24, 25, and temperature sensor 136, to an integrated chip or microprocessor and a power source, such as batteries, that allow system 10 to be used and programmed to measure a variety of electrochemical and optical properties of the water or other fluid being analyzed and to make calculations based on those measurements. The configuration of printed circuit board 14 shown in the figures is representative only of its relationship to electro-optical housing 12 and other components of the system 10. The circuit layout, other electronic components of the electronic module, and connections needed to allow system 10 to operate as described herein will be understood by those of ordinary skill in the art and are not depicted in the figures. The electronic module in system 10 permits the system to make various measurements, to communicate the results to a user to send signals to automatically control components of the fluid system being tested based on the measurements.

Most preferably, system 10 is configured to communicate to different devices and systems that provide feed-forward, feedback, automated, or manual control of the fluid system from which the sample being analyzed is obtained. System 10 sends control parameters to these devices and systems based on the analysis of the sample and certain predetermined and/or programmed values or ranges for the property measured or calculated by system 10 through the sample analysis. For example, system 10 may measure conductivity of a sample, which if above or below a certain threshold could trigger actions within a control system for the fluid system (either automatically or to be manually performed) to control the fluid system conductivity cycle. Depending on the measurement determined by system 10, the fluid system control means may either add more fresh make-up water to the fluid system or bleed more water out of the fluid system. As another example, system 10 may measure a concentration of a treatment chemical in the fluid system, which if above or below a certain threshold could trigger actions within a control system for the fluid system (either automatically or to be manually performed) to increase or decrease the feed rate of the treatment chemical. System 10 can also be configured to send signals to allow automatic or manual adjustments in treatment chemical feed rates in the fluid system based on fluorescence feedback (or other optical property) based on sample analysis using system 10. Additional examples for the use of system 10 to control operating parameters of a fluid system are described below.

When system 10 is ready to be used, the user simply fills the sample receptacle, defined by cell 80, optical module holder body 30 and 90, and at least part of recessed area 156 with a sample, uses buttons 15 or touch screen on control panel 20 to select the tests to be performed (preferably both an optical and electrochemical analysis are performed), the electronic module performs the selected tests substantially simultaneously and displays the results of each test or calculations based on those results on display 18. Additionally, the results of the optical analysis may be compared to the electrochemical analysis to achieve greater accuracy and better control of the fluid system.

For example, system 10 may be configured to measure the concentration of an optically active tracer added to a treatment chemical used in the fluid system by measuring the fluorescence, transmission or absorbance of light from a light source 22 or 23 through a sample of fluid from the fluid system. A fluorescent signal measured by system 10 from a fluid system sample would indicate the amount of treatment product pumped into the fluid system. Preferably, one of the light sources would be an LED-UV emitter that was designed to excite the tracer molecule and one of the sensors would be a photodiode detector with the appropriate bandpass filter to measure the emission signal at a right angle from the LED-UV source. The other light source and the other sensor may be used to measure the color and turbidity of the sample. Both properties are of interest in measuring or calculating concentrations of water treatment chemicals and can be used to compensate for fluctuations in the fluorescence measurement carried with the UV-LED and the corresponding detector. The electronic module of system 10 preferably receives signals from an optical detector or sensor 24 or 25 (or both, depending on what optical properties are being measured) and performs calculations to determine the concentration of the tracer, which may be used to calculate a concentration of the treatment product to which the tracer has been added.

System 10 may also be configured to measure the conductivity of the same sample using signals received from electrodes 26, 27, 28. The conductivity and optical measurements are performed by system 10 substantially simultaneously. The measured conductivity may then be used to calculate a concentration of the treatment product in the sample, with such calculations preferably being automatically performed by the electronic module of system 10. A comparison of the two concentration measurements may then be made to determine the difference or deviation percentage, either manually or, more preferably, automatically by system 10. The electronic module may then display the results of the comparison on display 18. Comparing a conductivity-based measurement and fluorescence-based measurement of the same property (such as concentration of treatment product and product dosage) improves the accuracy of controlling the fluid system. Using both an optically-based measurement and electrochemically-based measurement allows the operator to assure that the fluid system is operating at the proper cycles of concentration, and that the treatment chemicals are being added at a concentration needed to control corrosion and deposition at these same cycles. The cycles measured by conductivity can be used to evaluate the material dosage measured by fluorescence, and they can be used to further evaluate the conditions of the system.

In addition to measuring a variety of electrochemical and optical properties of a sample of the water or other fluid circulating in the fluid system, system 10 may also be used to measure conductivity (or other electrochemical and optical properties) of a sample from a source of make-up water or other fluid that may be periodically added to the fluid system. Using buttons 15 or a touch screen, a user may also input data designating whether a sample is from the fluid system or from a source of make-up water so that the conductivity (or other electrochemical and optical property) measurements may be differentiated. Based on those measurements, system 10 can calculate the conductivity cycle, which is the ratio of the conductivity of the sample from the make-up source (e.g. cooling tower make-up water) and the conductivity of the sample from the fluid system (e.g. from a cooling tower). That data may be used to modify operational parameters of the fluid system, such as a rate of blow-down and a rate of addition of make-up water, to bring the conductivity of the fluid circulating in the system to within a desired range. Similarly, some sources of makeup water exhibit a background fluorescence signal. By analyzing a sample of the make-up water for fluorescence using system 10, and designating that fluorescence measurement as the makeup background fluorescence, the fluorescence Measurement for the corresponding sample from the fluid in the fluid system (e.g. water circulating through the cooling tower) can be corrected according to the measured background. Preferably, system 10 can be programmed and configured to automatically make such corrections, if desired.

If any measured or calculated result, comparison of results, difference in results, or deviation is out of a predetermined or pre-set range of desired values for the specific property being measured or is above or below a predetermined or pre-set threshold value for the specific property or comparison of properties, then system 10 may generate an alarm (audible, visual, or both, and locally or remotely or both) that an adjustment or modification of one or more operating parameters for the fluid system is needed. Such adjustments may be performed manually, manually entered into the sensing system 10 to be communicated to a control system to automatically carry out the adjustment commands, or may be manually entered into a separate control system for the fluid system and then automatically carried out by that control system. Most preferably, system 10 is configured to automatically initiate such adjustments by sending signals to the control system or smart components within the fluid system, such as opening or closing valves, to alter one or more parameters of operation of the fluid system if one or more of the properties measured or compared is out of a first range of values specified for that property or is above or below a specified threshold. Adjustments in operating parameters may include altering the amount of treatment product added to the fluid system, adjusting blowdown rate, adjusting fresh-water make-up rate, increasing or decreasing flow rates through the fluid system, or other adjustments as needed to bring the fluid in the fluid system within desired ranges for various fluid properties calculated based on the optical and/or electrochemical measurements.

Once the desired tests are performed on a sample, system 10 is inverted to drain the sample into an appropriate drain or other receptacle for disposal. New tests are periodically performed by acquiring a new sample from the fluid system and/or make-up source and repeating the steps above. Most preferably, the results of measurements and comparisons are saved onto internal memory or a removable memory card or other external storage device so that historical data may be recalled and reviewed. Control buttons 15 or touch screen on control panel 20 may preferably be used to retrieve prior test results, which are displayed on display 18, for the user's review. The electronic module may be configured to display test results and comparisons on display 18 either numerically or graphically or both.

Figure 10:
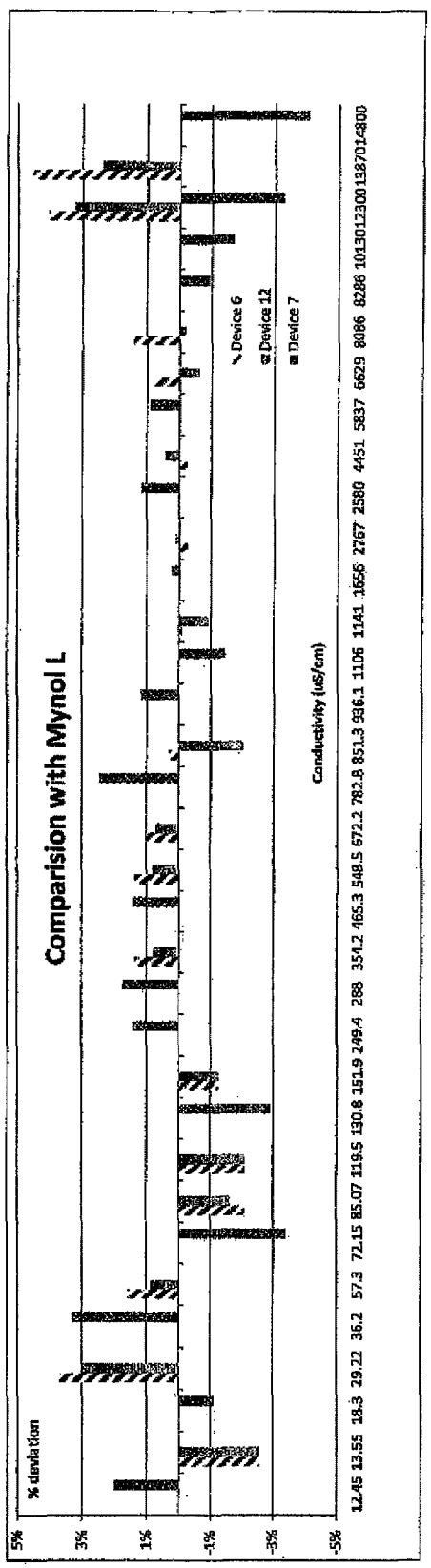
FIG. 10 is a graph showing percentages of deviation between conductivity results measured by devices according to a preferred embodiment of the invention and results measured by a commercially available conductivity meter.

Several sample devices (labeled as device #6, #7, and #12) according to a preferred embodiment of the invention were tested to determine the accuracy of both optical and electrochemical measurements. Conductivity was measured using three sample meters according to a preferred embodiment of the invention and using a commercially available Myron L conductivity meter. Below in Table 1 are the conductivity results at various reading levels using Myron L device and at least one of the test meters according to the invention, along with a calculation of percentage deviation between the measurements made by the devices according to the invention and that obtained by the Myron L device. The deviation percentages are also depicted in FIG. 10. The small amount of variation as compared to the Myron L device indicates that the meters according to a preferred embodiment of the invention are capable of accurately and consistently measuring conductivity.

TABLE 1

| MYRONL (uS/cm) | 6# (uS/cm) | 6# Deviation | 12# (uS/cm) | 12# Deviation | 7# (uS/cm) | 7# Deviation |
|---|---|---|---|---|---|---|
| 12.45 | | 0% | | 0% | 12.7 | 2% |
| 13.55 | 13.2 | -3% | 13.2 | -3% | | 0% |
| 18.3 | | 0% | | 0% | 18.1 | -1% |
| 29.22 | 30.3 | 4% | 30.1 | 3% | | 0% |
| 36.2 | | 0% | | 0% | 37.4 | 3% |
| 57.3 | 58.2 | 2% | 57.8 | 1% | | 0% |
| 72.15 | | 0% | | 0% | 69.7 | -3% |
| 85.07 | 83.3 | -2% | 83.7 | -2% | | 0% |
| 119.5 | 117 | -2% | 117 | -2% | | 0% |
| 130.8 | | 0% | | 0% | 127 | -3% |
| 151.9 | 150 | -1% | 150 | -1% | | 0% |
| 249.4 | | 0% | | 0% | 253 | 1% |
| 288 | | 0% | | 0% | 293 | 2% |
| 354.2 | 359 | 1% | 357 | 1% | | 0% |
| 465.3 | | 0% | | 0% | 472 | 1% |
| 548.5 | 556 | 1% | 553 | 1% | | 0% |
| 672.2 | 679 | 1% | 677 | 1% | | 0% |
| 782.8 | | 0% | | 0% | 802 | 2% |
| 851.3 | 854 | 0% | 834 | -2% | | 0% |
| 936.1 | | 0% | | 0% | 947 | 1% |
| 1106 | | 0% | | 0% | 1090 | -1% |
| 1141 | 1140 | 0% | 1130 | -1% | | 0% |
| 1656 | | 0% | | 0% | 1660 | 0% |
| 2767 | 2760 | 0% | 2770 | 0% | | 0% |
| 2580 | | 0% | | 0% | 2610 | 1% |
| 4451 | 4440 | 0% | 4470 | 0% | | 0% |
| 5837 | | 0% | | 0% | 5890 | 1% |
| 6629 | 6680 | 1% | 6590 | -1% | | 0% |
| 8086 | 8200 | 1% | 8070 | 0% | | 0% |
| 8286 | | 0% | | 0% | 8210 | -1% |
| 10130 | | 0% | | 0% | 9960 | -2% |
| 12300 | 12800 | 4% | 12700 | 3% | 11900 | -3% |
| 13870 | 14500 | 5% | 14200 | 2% | | 0% |
| 14800 | | 0% | | 0% | 14200 | -4% |

A test meter according to a preferred embodiment of the sensing system 10 of the invention was also used to measure fluorescence of samples containing PTSA (pyrene tertrasulphonic acid), which is a fluorescent tracer added to some commercially available cooling tower treatment products. Known quantities of PTSA were added to various samples of deionized water and water containing additives to simulate discoloration and turbidity that may be encountered in typical industrial water systems were tested. The quantity of PTSA expected, based on sample size and amount of PTSA added, was compared to the PTSA measurement from the meter and the results are listed below in Table 2. As can be seen, the measured results are very close to the expected results, which indicates that the meters according to a preferred embodiment of the invention are capable of accurately and consistently measuring fluorescence.

TABLE 2

| Sample Type | PTSA Expected/ppb | PTSA Measured/ppb |
|---|---|---|
| PTSA in Deionized Water | 100.0 | 102.0 |
| PTSA in Deionized Water | 200.0 | 199.1 |
| PTSA in Water Containing Simulated Color and Turbidity | 25.0 | 24.5 |
| PTSA in Water Containing Simulated Color and Turbidity | 50.0 | 42.7 |
| PTSA in Water Containing Simulated Color and Turbidity | 100.0 | 98.0 |
| PTSA in Water Containing Simulated Color and Turbidity | 100.0 | 97.6 |
| PTSA in Water Containing Simulated Color and Turbidity | 100.0 | 107.7 |

Sensing systems according to the invention, such as sensing system 10, may be used to measure multiple optical and electrochemical properties of a sample of water or other fluid from a fluid system to be tested. Changes in the optical components used (such as light sources 22, 23 and detectors 24, 25) may be needed for measuring different types of properties and electro-optical housing 12 can be modified to accommodate such different components. Additionally, the electronic module will require programming specific to the testing to be performed and may require different configurations, depending on the specific property being measured. Most typically, sensing system 10 will be used to measure absorbance, transmission, fluorescence, or turbidity, but other optical or light measurements may be possible using different optical component materials. Most typically, system 10 will also be used to measure conductivity, but other electrochemical properties, such as oxidation-reduction potential, may be measured.

References herein to calculating or measuring a value or property and the like are intended to include any form of direct measurement, converting data or a signal, making a calculation based on one or more data points or signals, or otherwise comparing, interpreting, correlating, or manipulating one or more data points or signals. Those of ordinary skill in the art will also appreciate upon reading this specification and the description of preferred embodiments herein that modifications and alterations to the system may be made within the scope of the invention and it is intended that the scope of the invention disclosed herein be limited only by the broadest interpretation of the appended claims to which the inventors are legally entitled.

We claim:

1. A portable device for detecting both optical and electrochemical properties of a fluid or fluid mixture, the device comprising:
    a sample receptacle for containing a sample of the fluid or fluid mixture;
    a first and a second light source for directing light to the sample receptacle;
    a first and a second optical sensor configured to detect an emission or transmission of light through the sample receptacle or from a compound in the sample;
    at least two electrodes, a portion of each disposed to contact the sample in the sample receptacle;
    an electronic system configured to receive a first signal from the first optical sensor, a second signal from the electrodes, a third signal from the second optical sensor, and to calculate a first property based on the first signal, a second property based on a second signal, and a third property based on the third signal, and to compare the first or third property with the second property;
    wherein the first property is a concentration of a chemical in the sample, a concentration of the compound, fluorescence, transmission, absorbance, turbidity, color, optical density, light scattering, or clarity of the sample; and
    wherein the second property is concentration of the chemical in the sample, conductivity, cyclic voltammetry to determine oxidation and reduction potentials, or open circuit potential of the sample.

2. The device of claim 1 wherein the third property is a concentration of a chemical in the sample, a concentration of the compound, fluorescence, transmission, absorbance, turbidity, color, optical density, light scattering, or clarity of the sample, and wherein the first and third properties are different from each other.

3. The device of claim 1 wherein the electronic system is configured to receive a fourth signal from the first optical sensor and a fifth signal from the second optical sensor and to calculate a fourth property based on the fourth signal and to calculate a fifth property based on the fifth signal.

4. The device of claim 3 wherein the fourth and fifth properties are a concentration of a chemical in the sample, a concentration of the compound, fluorescence, transmission, absorbance, turbidity, color, optical density, light scattering, or clarity of the sample.

5. The device of claim 4 wherein the first property is fluorescence and wherein one or more of the third, fourth or fifth properties is absorbance, color, or turbidity and wherein the electronic system corrects the calculated fluorescence based on one or more of the calculated third, fourth or fifth properties.

6. The device of claim 3;
wherein the first and fifth signals are based on light from the first light source and the third and fourth signals are based on light from the second light source.

7. The device claim 6 wherein the third property is fluorescence;
wherein one or more of the first, fourth, and fifth properties are absorbance, color, or turbidity; and
wherein the electronic system corrects the calculated fluorescence based on one or more of the first, fourth, or fifth properties.

8. The device of claim 1 further comprising a temperature sensor for measuring a temperature of the sample.

9. The device of claim 1 further comprising a power source.

10. The device of claim 9 wherein the power source is a battery or solar cells.

11. The device of claim 1 further comprising a connection between the electronic system and an external power source.

12. The device of claim 11 where the power source comprises a peripheral computer or communication device having an independent source of power or a direct connection to an alternating or direct current.

13. The device of claim 1 further comprising a display for displaying results of one or more of the calculated properties or one or more comparisons of the calculated properties.

14. The device of claim 1 wherein the electronic system comprises memory for storing results of the calculated properties.

15. The device of claim 1 further comprising a receptacle configured to receive a removable memory chip for storing results of the calculated properties measured, wherein the receptacle allows data to be transferred from the electronic system to the removable memory chip.

16. The device of claim 1 wherein the sample receptacle comprises a sample cell having an internal volume between 1 to 20 ml.

17. The device of claim 1 further comprising a housing for containing the first and second light sources, first and second optical sensors, electronic system, electrodes, and sample receptacle, wherein the housing has a length dimension less than about 10 inches and a width dimension less than about 5 inches.

18. The device of claim 1 wherein a portion of each electrode is disposed through a wall of the sample receptacle to allow contact with the sample.

19. The device of claim 1 wherein a portion of the first electrode is disposed as an external coating on the light source and a portion of the second electrode is disposed as an external coating on the optical sensor, wherein the external coatings are in contact with the sample.

20. The portable device of claim 1 wherein the electronic system comprises:

a circuit board; and
a microprocessor or an integrated chip.

21. The portable device of claim 1 wherein the first property is also compared to the third property.

22. The portable device of claim 1 wherein the sample receptacle is retained within the portable device when the sample is added and drained.

23. A method of determining properties of a fluid or fluid mixture, the method comprising:
placing a sample of the fluid or fluid mixture in a sample cell;
directing light from a first light source to the sample cell;
directing light from a second light source to the sample cell;
detecting an emission or transmission of light through the sample cell or from a compound in the sample with a first optical sensor and a second optical sensor;
measuring a change of electric potential between two of at least two electrodes in contact with the sample in the sample cell;
calculating a first property of the fluid based on the detected emission or transmission from the first optical sensor;
calculating a second property of the fluid based on measured change of electric potential;
calculating a third property of the fluid based on the detected emission or transmission from the second optical sensor;
comparing the first or third property with the second property; and
wherein the calculating and comparing steps are performed by an electronic system connected to the optical sensors and electrodes.

24. The method of claim 23 further comprising providing a single apparatus housing the sample cell, light sources, optical sensors, electrodes, and electronic system.

25. The method of claim 24 further comprising displaying results of the calculating steps on a display screen on the apparatus and wherein the first and second properties may be the same property or different properties.

26. The method of claim 24 further comprising removing the sample from the sample cell after the detecting and measuring steps and wherein the sample cell is retained in the apparatus during the placing and removing steps.

27. The method of claim 23 wherein the electronic system comprises:
a circuit board; and
a microprocessor or an, integrated chip.

28. The method of claim 23 wherein the first property is also compared to the third property.

29. A portable sensing system for detecting both optical and electrochemical properties of a fluid or fluid mixture, the system comprising:
a sample receptacle for containing a sample of the fluid or fluid mixture;
a first and a second light source for directing light to the sample receptacle;
a first optical sensor for detecting an emission or transmission of light through the sample receptacle or from a first compound in the sample that corresponds to a first property;
at least two electrodes, a portion of each disposed to contact the sample in the sample receptacle for measuring a change in electric potential that corresponds to a second property;
a second optical sensor for detecting an emission or transmission of light through the sample receptacle or from the first compound or a second compound in the sample that corresponds to a third property; and wherein the sensing system calculates the first, second, and third properties and compares at least one of the first and third properties with the second property.

30. The sensing system of claim 29 wherein the first property is a concentration of a first chemical in the sample, a concentration of the first compound, fluorescence, transmission, absorbance, turbidity, color, optical density, light scattering, or clarity of the sample;

wherein the second property is concentration of the first chemical in the sample, conductivity, cyclic voltammetry to determine oxidation and reduction potentials, or open circuit potential of the sample; and wherein the third property is a concentration of the first or a second chemical in the sample, a concentration of the first compound or the second compound, fluorescence, transmission, absorbance, turbidity, color, optical density, light scattering, or clarity of the sample, and wherein the first and third properties are different from each other.

31. The sensing system of claim 29 further comprising a display to provide a visual representation of the first property, second property, third property, or a comparison of one or more thereof.

32. The sensing system of claim 29 wherein the first property is based on light detected from the first light source;

the third property is based on light detected from the second light source;

the first optical sensor also detects an emission or transmission of light through the sample receptacle or from the first or second compound in the sample based on light from the second light source that corresponds to a fourth property;

the second optical sensor also detects an emission or transmission of light through the sample receptacle or from the first or the second compound in the sample based on light from the first light source that corresponds to a fifth property; and the sensing system calculates the fourth and fifth properties and compares at least one optical sensor based property with at least one electrode based property.

33. A method of determining properties of a fluid or fluid mixture, the method comprising:

placing a first sample of the fluid or fluid mixture in a sample cell;

directing light from a first light source to the sample cell;

directing light from a second light source to the sample cell;

detecting an emission or transmission of light through the sample cell or from a compound in the sample with a first optical sensor and a with second optical sensor;

measuring a change of electric potential between two of at least two electrodes in contact with the sample in the sample cell;

calculating a first property of the fluid or fluid mixture based on the detected emission or transmission from the first optical sensor;

calculating a second property of the fluid or fluid mixture based on the measured change of electric potential;

calculating a third property of the fluid or fluid mixture based on the detected emission or transmission from the second optical sensor;

comparing at least one of the first or third properties of the first sample to the third property of the first sample; and wherein the measuring, calculating, and comparing steps are carried out by a single handheld device that houses the sample cell, first and second light sources, first and second optical sensors, and electrodes.

34. The method of claim 33 further comprising displaying results of one or more of the calculated properties or one or more comparisons on a display screen on the handheld device.

35. The method of claim 33 wherein the first property is a concentration of a first chemical in the sample, a concentration of the first compound, fluorescence, transmission, absorbance, turbidity, color, optical density, light scattering, or clarity of the sample;

wherein the second property is concentration of the first chemical in the sample, conductivity, cyclic voltammetry to determine oxidation and reduction potentials, or open circuit potential of the sample; and wherein the third property is a concentration of the first or a second chemical in the sample, a concentration of the first compound or the second compound, fluorescence, transmission, absorbance, turbidity, color, optical density, light scattering, or clarity of the sample, and wherein the first and third properties are different from each other.

36. The method of claim 35 wherein at least one property of the first sample based on the first optical sensor is also compared to at least one property of the first sample based on the second optical sensor.

37. The method of claim 33 wherein the first property is based on light originating from the first light source and the third property is based on light originating from the second light source and further comprising:

calculating a fourth property of the fluid or fluid mixture based on the detected emission or transmission from the first optical sensor from light originating from the second light source; and calculating a fifth property of the fluid of fluid mixture based on the detected emission or transmission from the second optical sensor from light originating from the first light source.

38. The method of claim 33 further comprising removing the first sample from the sample cell and periodically repeating the steps with a new sample of the fluid or fluid mixture.

39. The method of claim 33 wherein the first sample is from a first source of the fluid or fluid mixture and further comprising removing the first sample from the sample cell after the calculating steps;

placing a second sample of a fluid or fluid mixture from a second source in the sample cell;

repeating one or more of the steps to calculate a first, second, or third properties of the second sample; and comparing or making a calculation based on at least one of the calculated properties from the first sample and at least one of the properties of the second sample.

40. The method of claim 39 wherein the first sample is water from a circulating water system, the second sample is from makeup water added to the circulating water system, the second property for the first and second samples is conductivity, and the conductivity of the first and second samples is used to calculate a conductivity cycle.

* * * * *